United States Patent [19]
Yandell

[11] Patent Number: 5,485,636
[45] Date of Patent: Jan. 23, 1996

[54] RAPE PROTECTIVE DEVICE

[76] Inventor: Clifford N. Yandell, 2056 50th Ave., Vero Beach, Fla. 32966

[21] Appl. No.: 363,926

[22] Filed: Dec. 27, 1994

[51] Int. Cl.[6] .................................................. A41B 9/00
[52] U.S. Cl. ............................ 2/406; 2/73; 2/400; 2/401; 2/407; 128/883; 600/38; 600/41
[58] Field of Search .................................. 2/56, 69, 69.5, 2/73, 400, 401, 402, 403, 405, 406, 408, 2.5, 407; 128/883, 884; 600/38, 41

[56] References Cited

U.S. PATENT DOCUMENTS

| 33,162 | 8/1861 | Reynolds | 128/883 |
|---|---|---|---|
| 104,117 | 6/1870 | Cook | 128/883 |
| 4,599,751 | 7/1986 | Bouwhuis | 128/883 X |
| 5,368,050 | 11/1994 | Donelan | 2/406 X |

FOREIGN PATENT DOCUMENTS 0664689  3/1988  Switzerland ............................ 600/38

Primary Examiner—Jeanette E. Chapman
Attorney, Agent, or Firm—Alvin S. Blum

[57] ABSTRACT

A rape preventing undergarment is formed from flexible cut-resistant cable and covered with fabric. The cable forms a crotch covering web with very small openings. Each side of the crotch covering web is attached to a leg encircling cable free at one end which can be wrapped around the thigh and then length adjusted and removably locked into a cable clasp at the front end of the crotch covering. A waist encircling cable is attached by cable to the rear of crotch covering and in front descends to also lock into one of the cable clasps. The cable clasps are arranged to both be locked by a single padlock. The device is easily adjusted to fit snugly so that it cannot be pulled aside, yet it is comfortable and easily removed when unlocked.

12 Claims, 2 Drawing Sheets

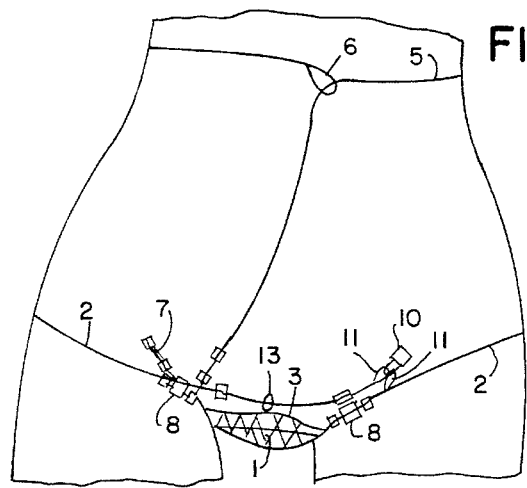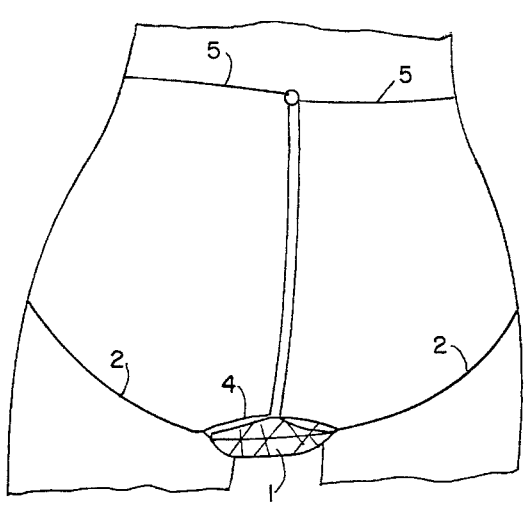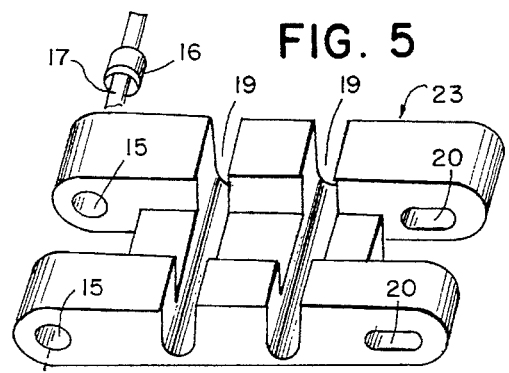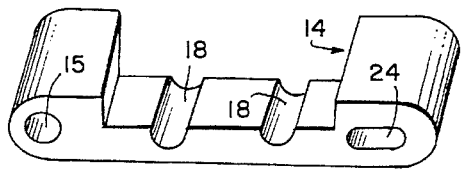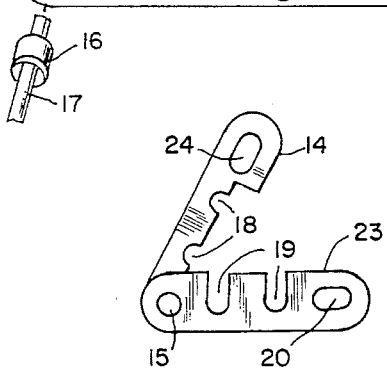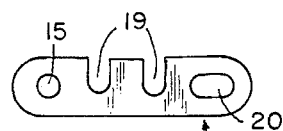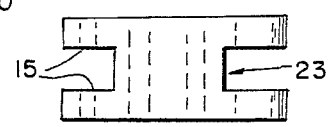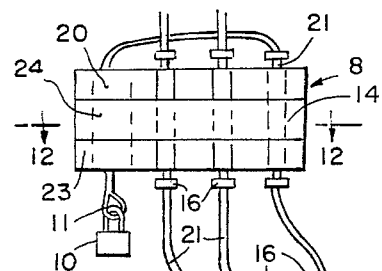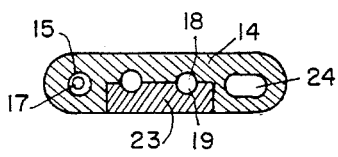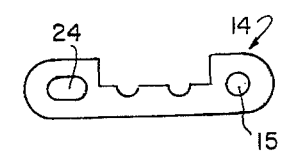

RAPE PROTECTIVE DEVICE

BACKGROUND OF THE INVENTION

This invention relates to protective clothing and more particularly to an undergarment for protecting a female from rape which is cut and tear resistant yet easily adjusted and comfortably worn.

It is well known that most rape of females is done by a friend or acquaintance. Date rape is most common, especially if one or both parties become inebriated or the male becomes persistent and forceful. If the female decides beforehand that she will not engage in intercourse, it would be very helpful if that determination could somehow be translated into a positive action that would prevent intercourse.

U.S. Pat. No. 4,599,751 issued Jul. 15, 1986 to Bouwhuis discloses a chain mail pants with close fitting legs and a lockable belt for this purpose. This would have to be custom fitted so that access could not be attained by pushing the garment aside at the legs. It would also be quite confining and uncomfortable.

SUMMARY OF THE INVENTION

It is accordingly an object of the invention to provide a protective garment that is readily adjusted to fit and effectively protect a user while being easily put on or removed for voiding or defecation. It is another object that the garment be well ventilated and comfortable while preventing unwanted access to the vulva or anus of the wearer even by forceful action. It is yet another object that access cannot be gained with a knife.

The garment of the invention comprises a network of cut resistant cable covering the vulva and anus connected to cables encircling both thighs and the waist.

The cables are so interconnected that a single lock can be used to prevent opening of the garment, when used with several unique cable clamps. The entire cable assembly is preferably enclosed within fabric for wearing comfort. It may be used over a conventional panty or in place of a panty. The cut resistant cable is preferably a multistranded stainless steel wire cable that is not readily cut unless a wire cutter is used. The lock may be a combination or key operated lock.

These and other objects, features and advantages of the invention will become more apparent when the detailed description is considered in conjunction with the drawings.

BRIEF DESCRIPTION OF THE DRAWINGS

FIG. 2 is a perspective anterior view of the device in use.

FIG. 3 is a perspective posterior view of the device in use.

FIG. 4 is a top view of the clasp in open position.

FIG. 5 is a perspective front elevation view of the outer portion of the clasp.

FIG. 6 is a top view of the outer portion of the clasp.

FIG. 7 is a rear elevation view of the outer portion of the clasp.

FIG. 8 is a perspective front elevation view of the inner portion of the clasp.

FIG. 9 is a top view of the inner portion of the clasp.

FIG. 10 is a rear elevation view of the inner portion of the clasp.

FIG. 11 is a front elevation view of the assembled and locked clasp.

FIG. 12 is a sectional view through line 12—12 of FIG. 11.

DETAILED DESCRIPTION OF PREFERRED EMBODIMENT

Figure 1:
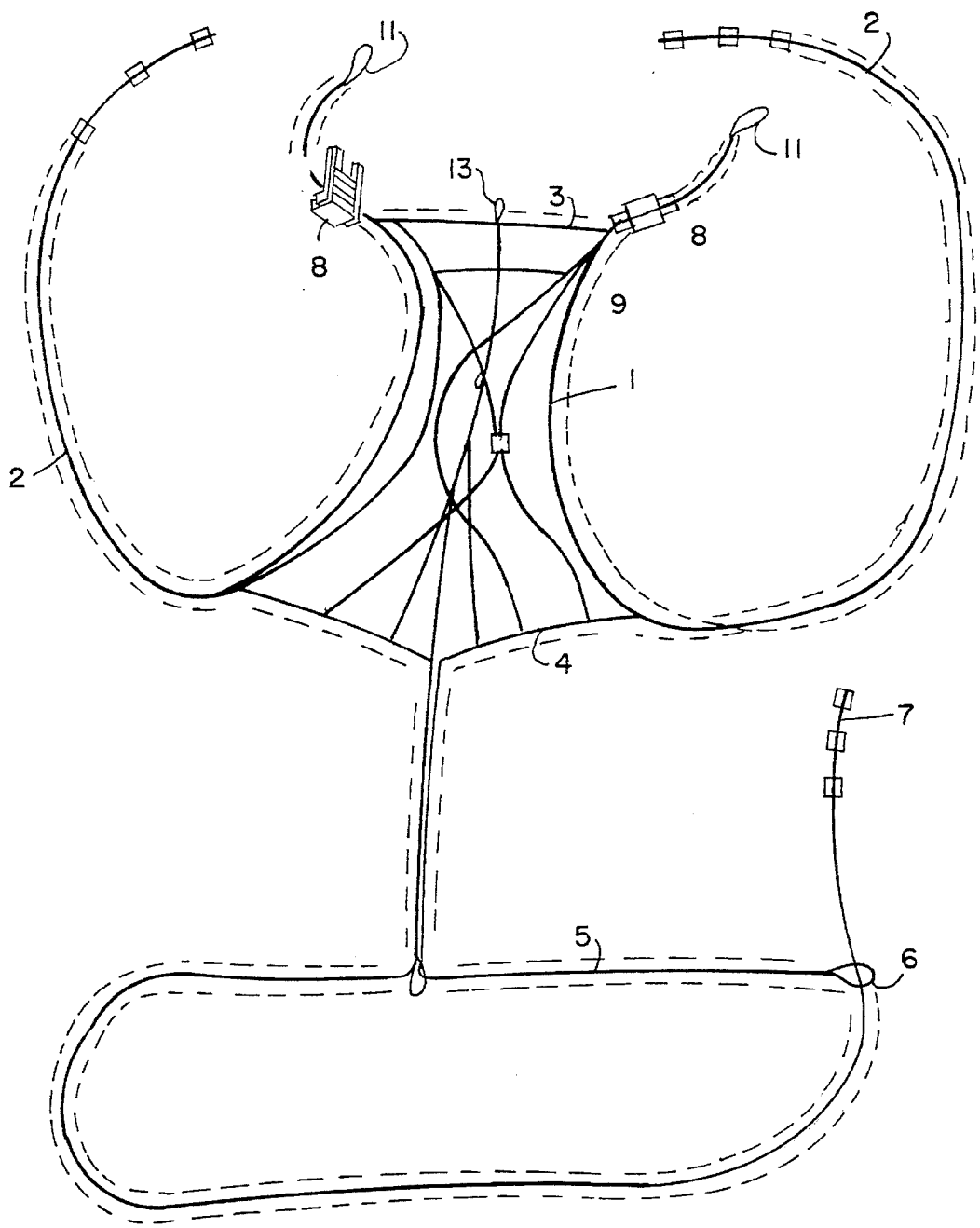
FIG. 1 is a plan view of the device unfastened.

Referring now first to FIGS. 1–3, the device comprises a web of interconnected stainless steel cables forming a crotch portion 1 for covering the vulva and anus so thoroughly that there are no openings in the web large enough for penis penetration. Two closable leg loops 2 are connected to the crotch portion so that upper front end 3 and rear end 4 of the crotch piece are held tight against the thighs when the leg loops are closed snugly against the thighs.

A waist loop 5 is connected at an intermediate point to the upper rear edge 4 of the crotch portion. One end terminates in a noose 6. The other end 7 is passed through the noose and fastens to one of the two cable clamps or clasps 8. Pulling down on the crotch only tightens the waist loop for additional security. The cable material is of a cut resistant and flexible nature with high tensile strength so as to prevent cutting or tearing away the protection. A multistranded stainless steel cable has been selected, but other cords or cables having these properties may also be employed. Except at the connecting ends, the cable material is preferably enclosed or sandwiched in a soft fabric 9 for comfort.

The fastening means shown herein provides great ease of adjustment for optimum security and comfort. It enables the wearer to put it on or take it off with a minimum of time and effort. It also enables the device to be secured with a single lock 10.

To don the garment, the waist loop is put in place with free end 7 hanging down in front. The crotch portion 1 is positioned between the legs and a first leg loop 2 is positioned around the leg from the rear and is held in place at a clasp 8 with a locking loop 11 locking the clasp. The second leg loop 2 is positioned around the second thigh and inserted in the second clasp 8. The free end 7 from the waist loop is also inserted in the second clasp 8 and that clasp is locked by the locking loop 11. Now the two locking loops are engaged by the padlock 10 along with loop 13 from the crotch portion, if desired. When the single padlock is closed, all of leg and waist loops are secured and the device cannot be easily removed or moved aside without opening the padlock.

Referring now to FIGS. 4–12, the cable clamp or clasp 8 is comprised of two separate pieces, an outer portion 23 and an inner portion 14. At one end is a pivot hole 15 which passes through both pieces. A cable 17 passes through this hole and is held in place by swaged sleeves 16 at both ends so that the clasp cannot be removed and the two pieces pivot on the pivot cable 17. There are two half slots 18 in the inner piece and corresponding half slots 19 in the outer piece. Two cables may be laid in these half slots from the side of the clasp when open. When the clasp is closed, pivoting about pivot cable 17, the two cables are held captive. When a locking cable with locking loop 11 is then slipped through slots 20 in the outer piece and slot 24 in the inner piece, the clasp is locked and the cables can only be removed by pulling out the locking loop 11. When the locking loops are held together by the padlock, the cables cannot be removed from the clasps because the locking cable cannot be pulled out of the slots 20, 24. The free end of one leg loop is locked in place in one of the half slots of each clasp. The free end 7 of the waist loop is also locked into one of the half slots in one of the clasps. By swaging on multiple sleeves 16, the cables are provided with length adjustments by simply inserting in the clasp an appropriate portion 21 of the cable between sleeves 16. The sleeves 16 are too large to pass through the hole formed by the juxtaposed half slots of the clasp.

The above disclosed invention has a number of particular features which should preferably be employed in combination although each is useful separately without departure from the scope of the invention. While I have shown and described the preferred embodiments of invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A protective undergarment for engaging both thighs and the waist of a wearer to prevent rape, the undergarment comprising:
   (A) cable interconnected to form a crotch cover means for covering the anus and vulva of a wearer with a web having no openings large enough for penetration by a penis, the crotch cover means having two opposed sides and front and rear upper edges;
   (B) a pair of cable clasp means for cable engaging, each one of said pair affixed to said crotch cover means at a junction of said front upper edge with one of said sides;
   (C) a pair of elongate leg cables, having a free end and a fixed end, each one of said pair having the fixed end attached to said crotch cover means at a junction of said rear upper edge with one of said sides;
   (D) said free end of each of said leg cables constructed for removably and length adjustably cooperating with one of said clasp means to snugly encircle a thigh while locking said leg cable within said clasp means to prevent loosening of the encirclement without disengaging said clasp means;
   (E) an elongate waist cable attached at an intermediate point thereof to said rear upper edge of said crotch cover means by a cable, said waist cable having a noose at a first end for passage therethrough of a second end to thereby adjustably and snugly encircle the waist, the second end constructed for removably and length adjustably cooperating with one of said clasp means to lock the second end of the waist cable within said clasp means;
   (F) locking means connected to said clasp means for preventing both of said clasp means from releasing said cables without the operation of said wearer; and
   (G) in which said cable is flexible, cut-resistant and stretch-resistant.

2. The undergarment according to claim 1, in which said cable is substantially covered by fabric.

3. The undergarment according to claim 2, in which said cable is stainless steel.

4. The undergarment according to claim 2, in which said clasp means is openable to receive cables, closable to retain cables, and lockable to prevent opening and release of said cables by passage therethrough of a locking loop on a cable.

5. The undergarment according to claim 4, in which each of said pair of clasp means is provided with a locking loop and the two locking loops are arranged to juxtapose when said clasp means are locked for engaging both loops with a single padlock.

6. The undergarment according to claim 5, in which said padlock is key operated.

7. The undergarment according to claim 5, in which said padlock is a combination lock.

8. A protective undergarment for engaging both thighs and the waist of a wearer to prevent rape, the undergarment comprising:
   (A) cable interconnected to form a crotch cover means for covering the anus and vulva of a wearer with a web having no openings large enough for penetration by a penis, the crotch cover means having two opposed sides and front and rear upper edges;
   (B) a pair of elongate leg cables, each leg cable having a fixed end and a free end, each fixed end attached to the crotch cover means at a junction of the rear upper edge with one of the sides;
   (C) a plurality of cable clasp means for secure cable engaging, one of the clasp means being affixed to the crotch cover means at each junction of the upper front edge thereof with one of the sides;
   (D) the free end of each leg cable being constructed for removably and length adjustably cooperating with one of the clasp means to snugly encircle a thigh while locking the leg cable within the clasp means to prevent loosening of the leg encirclement without opening of the clasp means;
   (E) an elongate waist encircling cable attached at an intermediate point thereof to the upper rear edge of the crotch cover means by a rear connecting cable and having at least one front connection cable to at least one leg cable, said waist encircling cable being adjustable for secure snug fitting about the waist of a wearer;
   (F) wherein the crotch cover means is arranged to securely cover the vulva and anus and prevent displacement therefrom when the leg cables are secured about legs and the waist encircling cable is secured about the waist and the clasp means are closed; and
   (G) lock means cooperating with the clasp means for preventing opening of the clasp means and removal or displacement of the crotch cover means without the wearer's cooperation.

9. The undergarment according to claim 8, in which the cable is substantially covered by fabric.

10. The undergarment according to claim 9, in which the cable is stainless steel.

11. The undergarment according to claim 9, in which the clasp means is openable to receive cables at a cable portion between cable enlargements, closable to retain cables, and lockable to prevent opening and release of the cables.

12. The undergarment according to claim 11, in which the clasp means is comprised of a first element hingedly joined to a second element by passage of a cable through an aperture in each element, each element being further provided with a complementary passage arranged to pass a cable with a locking loop therethrough so as to maintain the two elements in closed relationship when a locking loop is prevented from being pulled through the passages.

* * * * *